US005691303A

United States Patent [19]
Pan et al.

[11] Patent Number: 5,691,303
[45] Date of Patent: Nov. 25, 1997

[54] PERFUME DELIVERY SYSTEM COMPRISING ZEOLITES

[75] Inventors: Robert Ya-Lin Pan, Cincinnati; Jing-Feng You, West Chester; Gregory Stephen Caravajal, Fairfield, all of Ohio; Sharon Anne Graves; William Richard Mueller, both of Lawrenceburg, Ind.

[73] Assignee: The Procter & Gamble Company, Cincinnati, Ohio

[21] Appl. No.: 394,931

[22] Filed: Feb. 27, 1995

Related U.S. Application Data

[63] Continuation of Ser. No. 71,124, Jun. 2, 1993, abandoned.

[51] Int. Cl.$^6$ ...................................................... A61K 7/46
[52] U.S. Cl. ................................................ 512/4; 252/174.11
[58] Field of Search ............................................. 512/4

[56] References Cited

U.S. PATENT DOCUMENTS

| | | | |
|---|---|---|---|
| 4,190,551 | 2/1980 | Murata et al. | 252/99 |
| 4,209,417 | 6/1980 | Whyte | 252/174 |
| 4,304,675 | 12/1981 | Corey et al. | 252/8.6 |
| 4,326,967 | 4/1982 | Melville | 252/8.8 |
| 4,328,114 | 5/1982 | Johnson et al. | 252/135 |
| 4,339,356 | 7/1982 | Whyte | 252/522 |
| 4,347,152 | 8/1982 | Wixon | 252/174 |
| 4,394,127 | 7/1983 | Melville | 8/137 |
| 4,414,130 | 11/1983 | Cheng | 252/140 |
| 4,499,012 | 2/1985 | Farrell | 252/522 |
| 4,536,315 | 8/1985 | Ramachandran et al. | 512/4 |
| 4,539,135 | 9/1985 | Ramachandran et al. | 252/174 |
| 4,637,891 | 1/1987 | Delwel et al. | 252/135 |
| 4,713,193 | 12/1987 | Tai | 252/91 |
| 4,954,285 | 9/1990 | Wierenga et al. | 252/174.11 |
| 4,973,422 | 11/1990 | Schmidt | 512/4 |
| 5,011,690 | 4/1991 | Garvey et al. | 512/4 |
| 5,066,419 | 11/1991 | Walley et al. | 252/174 |
| 5,188,753 | 2/1993 | Schmidt | 512/4 |
| 5,336,665 | 8/1994 | Garner-Gray et al. | 512/4 |

FOREIGN PATENT DOCUMENTS

| | | | |
|---|---|---|---|
| 0535942A2 | 4/1993 | European Pat. Off. | C11D 3/00 |
| 0536942A2 | 4/1993 | European Pat. Off. | C11B 9/00 |
| 137599 | 9/1979 | Germany | C11D 206/798 |
| 248508 | 8/1987 | Germany | A61L 275/7324 |
| 64-1799 | 1/1989 | Japan | 512/4 |
| 3173565 | 7/1991 | Japan | 512/4 |
| HEI04-218583 | 8/1992 | Japan | C09K 3/00 |
| 2066839 | 7/1981 | United Kingdom | C11D 3/50 |

Primary Examiner—James H. Reamer
Attorney, Agent, or Firm—Brian M. Bolam; Kim William Zerby; Jerry J. Yetter

[57] ABSTRACT

Granular detergent compositions comprise conventional ingredients and a perfume delivery system which comprises Type X or Type Y Zeolites having a perfume releasably adsorbed within their pores, and a barrier matrix comprising a fluid polyol or diol which is insoluble with the perfume and a solid polyol containing more than three hydroxyl moieties. Methods of depositing said perfume onto fabric surfaces are disclosed.

12 Claims, No Drawings

PERFUME DELIVERY SYSTEM COMPRISING ZEOLITES

This is a continuation of application Ser. No. 08/071,124, filed On Jun. 2, 1993 now abandoned.

FIELD OF THE INVENTION

The present invention relates to perfume delivery systems and methods of using said perfume delivery systems in detergent compositions, especially granular detergents.

BACKGROUND OF THE INVENTION

Most consumers have come to expect scented laundry products and to expect that fabrics which have been laundered also to have a pleasing fragrance. Perfume additives make laundry compositions more aesthetically pleasing to the consumer, and in some cases the perfume imparts a pleasant fragrance to fabrics treated therewith. However, the amount of perfume carry-over from an aqueous laundry bath onto fabrics is often marginal. Industry, therefore, has long searched for an effective perfume delivery system for use in laundry products which provides long-lasting, storage-stable fragrance to the product, as well as fragrance to the laundered fabrics.

Laundry and other fabric care compositions which contain perfume mixed with or sprayed onto the compositions are well known from commercial practice. Because perfumes are made of a combination of volatile compounds, perfume can be continuously emitted from simple solutions and dry mixes to which the perfume has been added. Various techniques have been developed to hinder or delay the release of perfume from compositions so that they will remain aesthetically pleasing for a longer length of time. To date, however, few of the methods deliver significant fabric odor benefits after prolonged storage of the product.

Moreover, there has been a continuing search for methods and compositions which will effectively and efficiently deliver perfume from a laundry bath onto fabric surfaces. As can be seen from the following disclosures, various methods of perfume delivery have been developed involving protection of the perfume through the wash cycle, with release of the perfume onto fabrics. U.S. Pat. No. 4,096,072, Brock et al, issued Jun. 20, 1978, teaches a method for delivering fabric conditioning agents, including perfume, through the wash and dry cycle via a fatty quarternary ammonium salt. U.S. Pat. No. 4,402,856, Schnoring et al, issued Sep. 6, 1983, teaches a microencapsulation technique which involves the formulation of a shell material which will allow for diffusion of perfume out of the capsule only at certain temperatures. U.S. Pat. No. 4,152,272, Young, issued May 1, 1979, teaches incorporating perfume into waxy particles to protect the perfume through storage in dry compositions and through the laundry process. The perfume assertedly diffuses through the wax on the fabric in the dryer. U.S. Pat. No. 5,066,419, Walley et al, issued Nov. 19, 1991, teaches perfume dispersed with a water-insoluble nonpolymeric carrier material and encapsulated in a protective shell by coating with a water-insoluble friable coating material. U.S. Pat. No. 5,094,761, Trinh et al, issued Mar. 10, 1992, teaches a perfume/cyclodextrin complex protected by clay which provides perfume benefits to at least partially wetted fabrics.

Another method for delivery of perfume in the wash cycle involves combining the perfume with an emulsifier and water-soluble polymer, forming the mixture into particles, and adding them to a laundry composition, as is described in U.S. Pat. No. 4,209,417, Whyte, issued Jun. 24, 1980; U.S. Pat. No. 4,339,356, Whyte, issued Jul. 13, 1982; and U.S. Pat. No. 3,576,760, Gould et al, issued Apr. 27, 1971.However, even with the substantial work done by industry in this area, a need still exists for a simple, more efficient and effective perfume delivery system which can be mixed with laundry compositions to provide initial and lasting perfume benefits to fabrics which have been treated with the laundry product.

The perfume can also be adsorbed onto a porous carrier material, such as a polymeric material, as described in U.K. Pat. Pub. 2,066,839, Bares et al, published Jul. 15, 1981. Perfumes have also been adsorbed onto a clay or zeolite material which is then admixed into particulate detergent compositions. Generally, the preferred zeolites have been Type A or 4A Zeolites with a nominal pore size of approximately 4 Angstrom units. It is now believed that with Zeolite A or 4A, the perfume is adsorbed onto the zeolite surface with relatively little of the perfume actually absorbing into the zeolite pores. While the adsorption of perfume onto zeolite or polymeric carriers may perhaps provide some improvement over the addition of neat perfume admixed with detergent compositions, industry is still searching for improvements in the length of storage time of the laundry compositions without loss of perfume characteristics, in the intensity or amount of fragrance delivered to fabrics, and in the duration of the perfume scent on the treated fabric surfaces.

Another problem in providing perfumed products is the odor intensity associated with the products, especially high density granular detergent compositions. As the density and concentration of the detergent composition increase, the odor from the perfume components can become undesirably intense. A need therefore exists for a perfume delivery system which substantially releases the perfume odor during use but which does not provide an overly-intensive odor to the product, itself.

By the present invention it has now been discovered that certain zeolites with a nominal pore size of at least about 6 Angstroms effectively incorporate perfume into their pores. Without wishing to be limited by theory, it is believed that these zeolites provide a channel or cage-like structure in which the perfume molecules are trapped. Unfortunately, such perfumed zeolites are not sufficiently storage-stable for commercial use in granular fabric care products such as laundry detergents, particularly due to premature release of perfume upon moisture absorption. However, it has now also been discovered that the perfumed zeolite can then be matrixed with simple water-soluble, but perfume-insoluble, materials (such as sugars) which form a protective barrier entrapping and maintaining the perfume within the zeolite's pores. Thus, the perfume substantially remains in the matrix, even under humid conditions, without the need for expensive, complex coatings, encapsulations, or resin layers. It is also believed that since the perfume is incorporated into the relatively large zeolite pores, it has better perfume retention through the laundry process than other smaller pore size zeolites in which the perfume is predominately adsorbed on the zeolite surface. Fabrics treated by such perfume delivery systems thus have higher scent intensity and remain scented for longer periods of time after laundering.

The present invention solves the long-standing need for a simple, effective, storage-stable perfume delivery system which provides odor benefits during and after the laundering process, but which has reduced product odor during storage of the com- position. The present invention, after removal of the matrix in the wash, provides the additional, unexpected benefit of continued odor release when exposed to heat or humidity while being stored, dried or ironed.

BACKGROUND ART

U.S. Pat. No. 4,539,135, Ramachandran et al, issued Sep. 3, 1985, discloses particulate laundry compounds comprising a clay or zeolite material carrying perfume. U.S. Pat. No. 4,713,193, Tai, issued Dec. 15, 1987, discloses a free-flowing particulate detergent additive comprising a liquid or oily adjunct with a zeolite material. Japanese Patent HEI 4[1992]-218583, Nishishiro, published Aug. 10, 1992, discloses controlled-release materials including perfumes plus zeolites. U.S. Pat. No. 4,304,675, Corey et al, issued Dec. 8, 1981, teaches a method and composition comprising zeolites for deodorizing articles.

SUMMARY OF THE INVENTION

The present invention relates to a perfume delivery composition in the form of particles comprising:

a) from about 10% to about 90%, preferably from about 60% to about 80%, by weight, of a solid, water-insoluble, porous carrier which comprises a natural or synthetic zeolite having a nominal pore size of at least about 6 Angstroms;

b) a perfume which is releasably incorporated in the pores of said zeolite carrier to provide a perfumed zeolite; and c) from about 10% to about 90%, preferably from about 20% to about 40%, by weight, of a matrix coated on said perfumed zeolite which comprises a water-soluble (wash removable) composition in which the perfume is substantially insoluble, comprising from 0% to about 80%, by weight, of at least one solid polyol containing more than 3 hydroxyl moieties and from about 20% to about 100%, by weight, of a fluid diol or polyol in which the perfume is substantially insoluble and in which the solid polyol is substantially soluble.

The perfumed zeolite comprises from about 5% to about 30%, preferably from about 5% to about 20%, most preferably from about 7% to about 15%, by weight, of perfume and from about 70% to about 95%, preferably from about 80% to about 95%, most preferably from about 85% to about 93%, by weight, of zeolite. Preferred zeolites have a nominal pore size of at least about 6, preferably at least about 7 Angstroms, and a particle size no larger than about 120 microns, most preferably no larger than 30 microns. Preferred zeolites are faujasite-type zeolites selected from the group consisting of Zeolite X, Zeolite Y, and mixtures thereof. Typical, but non-limiting, examples of perfume ingredients employed in this invention include those selected from the group consisting of hexyl cinnamic aldehyde, benzyl benzoate, dihydromyrcenol, eugenol, heliotropin, coumarin, and mixtures thereof.

Preferred fluid diols and polyols used in the matrix are selected from the group consisting of glycerol, ethylene glycol, and diglycerol. Preferred solid polyols used in the matrix are selected from the group consisting of glucose, sorbitol, maltose, glucamine, sucrose, polyvinyl alcohol, starch, alkyl polyglycoside, sorbitan fatty ester, polyhydroxy fatty acid amides containing from about 1 to about 18, preferably from 1 to 12, most preferably from 1 to 8, carbon atoms in their fatty acid moieties, and mixtures thereof.

The perfume delivery particles are preferably in agglomerated form, said agglomerates being dissociable in water and having an average size of from about 200 microns to about 1000 microns, preferably from about 400 microns to about 600 microns. The agglomerated particles allow for admixing with detergent ingredients which have similar particle size.

The perfume delivery compositions herein can also be used in conventional detergent compositions, particularly in granular detergent compositions. The detergent composition will comprise from about 1% to about 20%, preferably from about 1% to about 8%, by weight, of said perfume delivery composition. The conventional detergent ingredients employed in fully-formulated detergent compositions provided herein can comprise from about 1% to about 99%, preferably from about 5% to about 80% of a detersive surfactant. Optionally, detergent compositions can comprise from about 5% to about 80% of a detersive builder. Other optional detergent ingredients can also be included in the fully-formulated detergent/perfume compositions provided by this invention. A second perfume can be sprayed onto the surface of said detergent granules, thereby providing fragrance to the product while it is stored.

The perfume delivery system of this invention is particularly effective in high density granular detergent compositions. Such concentrated granular detergent compositions typically have a bulk density of at least 550 grams/liter, preferably at least about 650 grams/liter, and ranging as high as about 900 grams/liter.

The method for depositing perfume on fabrics comprises contacting fabrics with an aqueous liquor containing at least about 1 ppm of said perfume delivery composition and, optionally, at least about 100 ppm of conventional detersive ingredients. Preferably, the aqueous liquor contains from about 10 ppm to about 200 ppm, most preferably from about 10 ppm to about 80 ppm, of the perfume delivery composition. The invention also encompasses a method for providing odor benefits on fabrics during storage, drying, or ironing comprising contacting fabrics with an aqueous liquor containing at least about 1 ppm, preferably from about 10 ppm to about 200 ppm, most preferably from about 10 ppm to about 80 ppm, of said perfume delivery composition and, optionally, at least about 100 ppm of conventional detersive ingredients, and drying the fabric in an automatic dryer, applying heat to fabrics which have been line-dried or machine dried at low heat by conventional ironing means (preferably with steam or pre-wet), or storing fabrics which have been line-dried or machine dried at low heat under ambient conditions with humidity (above about 20%).

The perfume delivery composition can be prepared in an anhydrous system by a process which comprises the steps of:

a) forming a perfumed zeolite by mixing porous, substantially dehydrated (less than 10%, preferably less than 5%, water) Zeolite X or Y with a perfume such that the perfume is incorporated into the pores of the zeolite;

b) forming a matrix by mixing a solid polyol containing more than 3 hydroxyl moieties with a fluid polyol or diol such as glycerol, ethylene glycol, or diglycerol to form a liquid; and c) mixing the matrix (b) with the perfumed zeolite (a) until free flowing particles are formed.

All percentages, ratios, and proportions herein are on a weight basis unless otherwise indicated. All documents cited are hereby incorporated by reference.

DETAILED DESCRIPTION OF THE INVENTION

The present invention relates to a perfume delivery system comprising a dehydrated zeolite, preferably Type X Zeolite, Type Y Zeolite, or a mixture thereof, wherein a perfume or a mixture of perfume and perfume fixative has been releasably absorbed in the pores of said zeolite. The perfumed zeolite is incorporated, in the absence of water, with a matrix preferably comprising a fluid diol or polyol and a solid polyol. The perfume delivery system is especially useful in granular detergent compositions.

The component materials are described below.

Perfume

As used herein the term "perfume" is used to indicate any pleasant smelling, odoriferous material which can be absorbed into the pores of the zeolites herein and which is subsequently released into the aqueous bath and/or onto fabrics contacted therewith. The perfume selected should be immiscible with the matrix materials employed in the perfume delivery system so as to limit loss of the perfume before use. The perfume will most often be liquid at ambient temperatures. A wide variety of chemicals are known for perfume uses, including materials such as aldehydes, ketones and esters. More commonly, naturally occurring plant and animal oils and exudates comprising complex mixtures of various chemical components are known for use as perfumes. The perfumes herein can be relatively simple in their compositions or can comprise highly sophisticated complex mixtures of natural and synthetic chemical components, all chosen to provide any desired odor. Typical perfumes can comprise, for example, woody/earthy bases containing exotic materials such as sandalwood, civet and patchouli oil. The perfumes can be of a light floral fragrance, e.g., rose extract, violet extract, and lilac. The perfumes can also be formulated to provide desirable fruity odors, e.g., lime, lemon, and orange. Any chemically compatible material which exudes a pleasant or otherwise desirable odor can be used in the perfumed compositions herein.

Examples of perfume ingredients deliverable by this invention include: hexyl cinnamic aldehyde, benzyl benzoate, dihydromyrcenol, eugenol, heliotropin, coumarin, and mixtures thereof.

Perfume Fixative

Optionally, the perfume can be combined with a perfume fixative. The perfume fixative materials employed herein are characterized by several criteria which make them especially suitable in the practice of this invention. Dispersible, toxicologically-acceptable, non-skin irritating, inert to the perfume, degradable and/or available from renewable resources, and relatively odorless additives are used. Perfume fixatives are believed to slow the evaporation of more volatile components of the perfume.

Examples of suitable fixatives include members selected from the group consisting of diethyl phthalate, musks, and mixtures thereof. If used, the perfume fixative comprises from about 10% to abut 50%, preferably from about 20% to about 40%, by weight, of the perfume.

Zeolites

The term "zeolite" used herein refers to a crystalline aluminosilicate material. The structural formula of a zeolite is based on the crystal unit cell, the smallest unit of structure represented by $$M_{m/n}[(AlO_2)_m(SiO_2)_y] \cdot xH_2O$$

where n is the valence of the cation M, x is the number of water molecules per unit cell, m and y are the total number of tetra-hedra per unit cell, and y/m is 1 to 100. Most preferably, y/m is 1 to 5. The cation M can be Group IA and Group IIA elements, such as sodium, potassium, magnesium, and calcium.

In general, the zeolite material useful in the present invention encompasses water-insoluble aluminosilicate particles with high adsorption efficiency, and a nominal pore size of at least about 6 Angstroms which is larger than the transverse axial dimension of the perfume and optional perfume fixative molecules that are to be absorbed in the porous material but which is capable of retaining the perfume in the zeolite structure while being stored. Pore volumes and pore size distributions may be measured by the recognized techniques of adsorption of sorbates of progressively increasing molecular diameter and by x-ray crystallography.

Contrary to the teachings of previous references, such as U.S. Pat. No. 4,304,675, and U.S. Pat. No. 4,539,135, both cited above, the use of Zeolite A or 4A is believed to have pore sizes too small (4 Angstroms or less) for effective absorption of the perfume molecules. Thus, it is believed that the perfume incorporated on type A or 4A Zeolites will rapidly dissipate from the zeolites during wash. Hence, compositions comprising such zeolites are not acceptable for effective carry-over of the perfume onto the fabrics which have been treated with them.

The preferred zeolite useful herein is a faujasite-type zeolite, including Type X Zeolite or Type Y Zeolite, both with a nominal pore size of about 8 Angstrom units, typically in the range of from about 7.4 to about 10 Angstrom units.

The aluminosilicate zeolite materials useful in the practice of this invention are commercially available. The zeolites useful in this invention can be crystalline or amorphous in structure and can be naturally-occurring aluminosilicates or synthetically derived. Methods for producing X and Y-type zeolites are well-known and available in standard texts. Preferred synthetic crystalline aluminosilicate materials useful herein are available under the designation Type X or Type Y.

For purposes of illustration and not by way of limitation, in a preferred embodiment, the crystalline aluminosilicate material is Type X and is selected from the following:

(I) $Na_{86}[AlO_2]_{86} \cdot (SiO_2)_{106}] \cdot xH_2O$, (II) $K_{86}[AlO_2]_{86} \cdot (SiO_2)_{106}] \times xH_2O$, (III) $Ca_{40}Na_6[AlO_2]_{86} \cdot (SiO_2)_{106}] \cdot xH_2O$, (IV) $Sr_{21}Ba_{22}[AlO_2]_{86} \cdot (SiO_2)_{106}] \cdot xH_2O$, and mixtures thereof, wherein x is from about 0 to about 276. Zeolites of Formula (I) and (II) have a nominal pore size or opening of 8.4 Angstroms units. Zeolites of Formula (III) and (IV) have a nominal pore size or opening of 8.0 Angstroms units.

In another preferred embodiment, the crystalline aluminosilicate material is Type Y and is selected from the following:

(V) $Na_{56}[AlO_2]_{56} \cdot (SiO_2)_{136}] \cdot xH_2O$, (VI) $K_{56}[AlO_2]_{56} \cdot (SiO_2)_{136}] \cdot xH_2O$ and mixture thereof, wherein x is from about 0 to about 276. Zeolites of Formula (V) and (VI) have a nominal pore size or opening of 8.0 Angstroms units.

Zeolites used in the present invention are in particle form having an average particle size from about 0.5 microns to about 120 microns, preferably from about 0.5 microns to about 30 microns, as measured by standard particle size analysis technique.

The size of the zeolite particles allows them to be entrained in the fabrics with which they come in contact. Once established on the fabric surface (with their coating matrix having been washed away during the laundry process), the zeolites can begin to release their perfume, especially when subjected to heat or humid conditions.

Incorporation of perfume in Zeolite—Type X or Type Y Zeolites are first activated/dehydrated by heating to about 150°–350° C., optionally with reduced pressure (from about 0.001 to about 20 Torr), for at least 12 hours. After activation, the perfume is slowly and thoroughly mixed with the activated zeolite and, optionally, heated to about 60° C. for about 2 hours to accelerate absorption equilibrium within the zeolite particles. The perfume/zeolite mixture is then cooled to room temperature and is in the form of a free-flowing powder.

Matrix

The matrix employed in the Perfume delivery system of this invention comprises a fluid diol or polyol, such as glycerol, ethylene glycol, or diglycerol (suitable fluid diols and polyols typically have a M.P. below about −10° C.) and, optionally but preferably, a solid polyol containing more than three hydroxyl moieties, such as glucose, sorbitol, and other sugars. The solid polyol should be dissolvable with heating in the fluid diol or polyol to form a viscous (approximately 4000 cPs), fluid matrix (i.e., the consistency of honey). The matrix, which is insoluble with the perfume, is thoroughly mixed with the perfumed zeolite and, thereby, entraps and "protects" the perfume in the zeolite. Solubility of the matrix in water enables the perfumed zeolite to be released in the aqueous bath during laundering.

The preferred properties of the matrix formed by the fluid diol or polyol and the solid polyol include strong hydrogen-bonding which enables the matrix to attach to the zeolite at the siloxide sites and to compete with water for access to the zeolite; incompatibility of the matrix with the perfume which enables the matrix to contain the perfume molecules inside the zeolite cage and to inhibit diffusion of the perfume out through the matrix during dry storage; hydrophilicity of the matrix to enable the matrix materials to dissolve in water for subsequent perfume release from the zeolites; and humectancy which enables the matrix to serve as a limited water sink to further protect the perfumed zeolite from humidity during storage.

The matrix material comprises from about 20% to about 100%, preferably from about 50% to about 70%, by weight of the fluid diol or polyol and from 0% to about 80%, preferably from about 30% to about 50%, by weight, of one or more solid polyols. Of course, the proportions can vary, depending on the particular solid polyols and fluid polyols that are chosen. The perfume delivery system comprises from about 10% to about 90%, preferably from about 20% to about 40%, by weight of the diol/polyol matrix material, the balance comprising the perfume-plus-zeolite.

In addition to its function of containing/protecting the perfume in the zeolite particles, the matrix material also conveniently serves to agglomerate multiple perfumed zeolite particles into agglomerates having an overall particles size in the range of 200 to 1000 microns, preferably 400 to 600 microns. This reduces dustiness. Moreover, it lessens the tendency of the smaller, individual perfumed zeolites to sift to the bottom of containers filled with granular detergents, which, themselves, typically have particle sizes in the range of 200 to 1000 microns.

The following nonlimiting example describes a typical laboratory preparation of the perfume delivery composition.

EXAMPLE I

About 119 g of Zeolite 13X powder is activated/dehydrated at 200° C. at 14 Torr for about 24 hours. The activated zeolite (119 g) is added to a glass vessel, and 21 g of perfume (any commercial perfume is useful; Alba-C is typical) is slowly added with thorough mixing and shaking to yield an 85/15 zeolite:perfume ratio. The zeolite/perfume mixture is transferred to a mixer (Cuisinart) and mixed for approximately 20 seconds. The mixture is then returned to a glass vessel. The vessel is sealed and vibrated to compact the sample. The zeolite/perfume mixture is heated in the closed vessel at 60° C. for 2 hours, and then cooled to room temperature.

In another glass vessel, 34.3 g of anhydrous glycerol is heated to approximately 110°–120° C. with continuous stirring. To the glycerol is added 25.7 g of anhydrous glucose to yield a 42.5:57.5 ratio of glycerol to glucose. Heating and stirring are continued until a clear, liquid solution is formed. The solution is cooled to room temperature.

To a large, flat crystallizing dish, first add the 60 g of glycerol/glucose solution, and then add the 140 g of zeolite/perfume. The solid zeolite/perfume is thoroughly mixed with the viscous liquid solution and transferred to a Cuisinart mixer for approximately 3 minutes of agitation. The resulting product, which is in the form of a free-flowing powder agglomerate, is then transferred to a container and sealed for storage.

The perfume delivery compositions are used in compositions with detersive ingredients, as follows.

Conventional Detersive Ingredients Detersive Surfactant

The amount of detersive surfactant included in the conventional detergent ingredients employed in the present invention can vary from about 1% to about 99% by weight of the detergent composition depending upon the particular surfactant(s) used and the effects desired. Preferably, the detersive surfactant(s) comprises from about 5% to about 80% by weight of the composition.

The detersive surfactant can be nonionic, anionic, ampholytic, zwitterionic, or cationic. Mixtures of these surfactants can also be used. Preferred detergent compositions, therefore, comprise anionic detersive surfactants or mixtures of anionic surfactants with other surfactants disclosed herein.

Nonlimiting examples of surfactants useful herein include the conventional $C_{11}$–$C_{18}$ alkyl benzene sulfonates and primary, secondary, and random alkyl sulfates, the $C_{10}$–$C_{18}$ alkyl alkoxy sulfates, the $C_{10}$–$C_{18}$ alkyl polyglycosides and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetatnes ("sultaines"), $C_{10}$–$C_{18}$ amine oxides, and the like. Other conventional useful surfactants are listed in standard texts.

One particular class of adjunct nonionic surfactants especially useful herein comprises the polyhydroxy fatty acid amides of the formula:

 (I)

wherein: $R^1$ is H, $C_1$–$C_8$ hydrocarbyl, 2-hydroxyethyl, 2-hydroxy-propyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{32}$ hydrocarbyl moiety, preferably straight chain $C_9$–$C_{17}$ alkyl or alkenyl, more preferably straight chain $C_9$–$C_{17}$ alkyl or alkenyl, most preferably straight chain $C_{11}$–$C_{19}$ alkyl or alkenyl, or mixture thereof; and Z is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —CH($CH_2OH$)—$(CHOH)_{n-1}$—$CH_2OH$, —$CH_2$—$(CHOH)_2$(CHOR')—(CHOH)—$CH_2OH$, where n is an integer from 1 to 5, inclusive, and R' is H or a cyclic mono- or polysaccharide, and alkoxylated derivatives thereof. Most preferred are glycityls wherein n is 4, particularly —$CH_2$—$(CHOH)_4$—$CH_2OH$.

In surfactant formula (I), $R^1$ can be, for example, N-methyl, N-ethyl, N-propyl, N-isopropyl, N-butyl, N-isobutyl, N-2-hydroxy ethyl, or N-2-hydroxy propyl. For highest sudsing, $R^1$ is preferably methyl or hydroxyalkyl. If lower sudsing is desired, $R^1$ is preferably $C_2$–$C_8$ alkyl, especially n-propyl, iso-propyl, n-butyl, iso-butyl, pentyl, hexyl and 2-ethyl hexyl.

$R^2$—CO—N< can be, for example, cocamide, stearamide, oleamide, lauramide, myristamide, capricamide, palmitamide, tallowamide, etc. (It is to be understood that separate portions of the poly- hydroxy fatty acid amides can be used both as the detersive sur- factant in the detergent compositions herein, and as the solid polyol of the matrix material used to coat the preferred zeolites.)

Detersive Builders

Other conventional detersive ingredients optionally employed in the present invention include inorganic and/or organic detersive builders to assist in mineral hardness control. Typically, these builders will comprise from about 5% to about 80% by weight of the detergent compositions.

Inorganic detersive builders include, but are not limited to, the alkali metal, ammonium and alkanolammonium salts of polyphosphates (exemplified by the tripolyphosphates, pyrophosphates, and glassy polymeric meta-phosphates), phosphonates, silicates, carbonates (including bicarbonates and sesquicarbonates), sulphates, and aluminosilicates. However, non-phosphate builders are required in some locales.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck.

Examples of carbonate builders are the alkaline earth and alkali metal carbonates as disclosed in German Patent Application No. 2,321,001 published on Nov. 15, 1973.

Aluminosilicate builders are useful in the present invention. Preferred aluminosilicates are zeolite builders which have the formula:

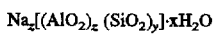

wherein z and y are integers of at least 6, the molar ratio of z to y is in the range from 1.0 to about 0.5, and x is an integer from about 15 to about 264. Such builders are Type A or 4A Zeolites, as distinguished from the Type X or Type Y Zeolites used to carry the perfume.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A and Zeolite P (B). Preferably, the aluminosilicate has a particle size of about 0.1–10 microns in diameter.

Organic detersive builders suitable for the purposes of the present invention include, but are not restricted to, a wide variety of polycarboxylate compounds, such as ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987.

Other useful detergency builders include the ether hydroxy-polycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders that can also be used in detergent compositions, especially in combination with zeolite and/or layered silicate builders.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Optional Detersive Adjuncts

As a preferred embodiment, the conventional detergent ingredients employed herein can be selected from typical detergent composition components such as detersive surfactants and detersive builders. Optionally, the detergent ingredients can include one or more other detersive adjuncts or other materials for assisting or enhancing cleaning performance, treatment of the substrate to be cleaned, or to modify the aesthetics of the detergent composition. Usual detersive adjuncts of detergent compositions include the ingredients set forth in U.S. Pat. No. 3,936,537, Baskerville et al. Such adjuncts which can be included in detergent compositions employed in the present invention, in their conventional art-established levels for use (generally from 0% to about 80% of the detergent ingredients, preferably from about 0.5% to about 20%), include color speckles, suds boosters, suds suppressors, anti-tarnish and/or anticorrosion agents, soil-suspending agents, soil release agents, dyes, fillers, optical brighteners, germicides, alkalinity sources, hydrotropes, antioxidants, enzymes, enzyme stabilizing agents, solvents, solubilizing agents, chelating agents, clay soil removal/anti-redeposition agents, polymeric dispersing agents, processing aids, fabric softening components, static control agents, bleaching agents, bleaching activators, bleach stabilizers, etc.

High Density Granular Detergent Composition

The perfume delivery composition can be used in both low density (below 550 grams/liter) and high density granular detergent compositions in which the density of the granule is at least 550 grams/liter. Such high density detergent compositions typically comprise from about 30% to about 90% of detersive surfactant.

Low density compositions can be prepared by standard spray-drying processes. Various means and equipment are available to prepare high density granular detergent compositions. Current commercial practice in the field employs spray-drying towers to manufacture granular laundry detergents which often have a density less than about 500 g/l. Accordingly, if spray drying is used as part of the overall process, the resulting spray-dried detergent particles must be further densified using the means and equipment described hereinafter. In the alternative, the formulator can eliminate spray-drying by using mixing, densifying and granulating equipment that is commercially available. The following is a nonlimiting description of such equipment suitable for use herein.

High speed mixer/densifiers can be used in the present process. For example, the device marketed under the trademark "Lodige CB30" Recycler comprises a static cylindrical mixing drum having a central rotating shaft with mixing/cutting blades mounted thereon. Other such apparatus includes the devices marketed under the trademark "Shugi Granulator" and under the trademark "Drais K-TTP 80". Equipment such as that marketed under the trademark "Lodige KM600 Mixer" can be used for further densification.

In one mode of operation, the compositions are prepared and densified by passage through two mixer and densifier machines operating in sequence. Thus, the desired compositional ingredients can be admixed and passed through a Lodige mixture using residence times of 0.1 to 1.0 minute then passed through a second Lodige mixer using residence times of 1 minute to 5 minutes.

In another mode, an aqueous slurry comprising the desired formulation ingredients is sprayed into a fluidized bed of particulate surfactants. The resulting particles can be further densified by passage through a Lodige apparatus, as noted above. The perfume delivery particles are admixed with the detergent composition in the Lodige apparatus.

The final density of the particles herein can be measured by a variety of simple techniques, which typically involve dispensing a quantity of the granular detergent into a container of known volume, measuring the weight of detergent and reporting the density in grams/liter.

Once the low or high density granular detergent "base" composition is prepared, the agglomerated perfume delivery system of this invention is added thereto by any suitable dry-mixing operation.

Deposition of Perfume onto Fabric Surfaces

The method of washing fabrics and depositing perfume thereto comprises contacting said fabrics with an aqueous wash liquor comprising at least about 100 ppm of conventional detersive ingredients described hereinabove, as well as at least about 1 ppm of the above-disclosed perfume delivery system. Preferably, said aqueous liquor comprises from about 500 ppm to about 20,000 ppm of the conventional detersive ingredients and from about 10 ppm to about 200 ppm of the perfume delivery system.

The perfume delivery system works under all circumstances, but is particularly useful for providing odor benefits on fabrics during storage, drying or ironing. The method comprises contacting fabrics with an aqueous liquor containing at least about 100 ppm of conventional detersive ingredients and at least about 1 ppm of the perfume delivery composition such that the perfumed zeolite particles are entrained on the fabrics, storing line-dried fabrics under ambient conditions with humidity of at least 20%, drying the fabric in a conventional automatic dryer, or applying heat to fabrics which have been line-dried or machine dried at low heat (less than about 50° C.) by conventional ironing means (preferably with steam or pre-wetting).

The following nonlimiting examples illustrate the parameters of and compositions employed within the invention. All percentages, parts and ratios are by weight unless otherwise indicated.

EXAMPLE II

A granular detergent composition is prepared comprising the following ingredients.

| Component | Weight % |
|---|---|
| $C_{12}$ linear alkyl benzene sulfonate | 22 |
| Phosphate (as sodium tripolyphosphate) | 30 |
| Sodium carbonate | 14 |
| Sodium silicate | 3 |
| Sodium percarbonate | 5 |
| Ethylenediamine disuccinate chelant (EDDS) | 0.4 |
| Sodium sulfate | 5.5 |
| Perfume Delivery System (Example I) | 3.0 |
| Nonanoyloxybenzenesulfonate | 5 |
| Minors, filler* and water | Balance to 100% |

*Can be selected from convenient materials such as $CaCO_3$, talc, clay, silicates, and the like.

An aqueous crutcher mix of heat and alkali stable components of the detergent composition is prepared and spray-dried. The other ingredients, including the perfume delivery system, are admixed in the final composition so that the composition contains the ingredients tabulated at the levels shown.

The detergent granules are added together with 5 lb. (2.3 kg) of previously laundered fabrics to an automatic washing machine to provide a detergent concentration of 1000 ppm in the 17 gallon (65 l) water-fill machine. Fabrics laundered with the composition and dried have a noticeable perfume fragrance. The fragrance intensity is still unchanged approximately 6 days after drying of the fabrics at 60°–70° C. for 40 minutes.

EXAMPLE III

A granular detergent composition is prepared comprising the following ingredients.

| Component | Weight % |
| --- | --- |
| Anionic alkyl sulfate | 7 |
| Nonionic surfactant | 5 |
| Zeolite A (0.1–10 micron) | 10 |
| Trisodium citrate | 2 |
| SKS-6 silicate builder | 10 |
| Acrylate maleate polymer | 4 |
| Sodium carbonate | 5 |
| Ethylenediamine disuccinate chelant (EDDS) | 0.4 |
| Perfume Delivery System (Example I) | 4.0 |
| Suds suppressor | 2 |
| Enzymes* | 1.5 |
| Soil release agent | 0.2 |
| Minors, filler** and water | Balance to 100% |

*1:1:1 mixture of protease, lipase, and cellulase.
**Can be selected from convenient materials such as CaCO₃, talc, clay, silicates, and the like.

An aqueous crutcher mix of heat and alkali stable components of the detergent composition is prepared and spray-dried. The other ingredients, including the perfume delivery system, are admixed therewith so that the final composition contains the ingredients tabulated at the levels shown.

The detergent granules are added via the dispensing drawer together with 5 lb. (2.3 kg) of previously laundered fabrics to an automatic washing machine. Actual weight of detergent composition is taken to provide an 8,000 ppm concentration in the 17 l water-fill machine. Fabrics laundered with the composition and line-dried have a noticeable perfume fragrance after either ironing or storage.

EXAMPLE IV

A laundry bar comprises the following.

| Component | Weight % |
| --- | --- |
| C₁₂ linear alkyl benzene sulfonate | 30 |
| Phosphate (as sodium tripolyphosphate) | 7 |
| Sodium carbonate | 25 |
| Sodium pyrophosphate | 7 |
| Coconut monoethanolamide | 2 |
| Zeolite A (0.1–10 micron) | 5 |
| Carboxymethylcellulose | 0.2 |
| Ethylenediamine disuccinate chelant (EDDS) | 0.4 |
| Polyacrylate (m.w. 1400) | 0.2 |
| Nonanoyloxybenzenesulfonate | 5 |
| Sodium percarbonate* | 5 |
| Brightener | 0.2 |
| Perfume delivery system (Example I) | 3.0 |
| Protease | 0.3 |
| CaSO₄ | 1 |
| MgSO₄ | 1 |
| Water | 4 |
| Filler** | Balance to 100% |

*Average particle size of 400 to 1200 microns.
**Can be selected from convenient materials such as CaCO₃, talc, clay, silicates, and the like.

The detergent laundry bar is extruded in conventional soap or detergent bar making equipment as commonly used in the art. Testing is conducted following the testing methods in Example II. Fabrics laundered with the composition and line-dried have a noticeable perfume fragrance after ironing or storage.

EXAMPLE V

A high density granular detergent comprises the following.

| Component | Weight % |
| --- | --- |
| C₁₂₋₁₄ linear alkyl benzene sulfonate | 15 |
| Sodium citrate | 5 |
| Sodium carbonate | 20 |
| Zeolite A (0.1–10 micron) | 26 |
| Brightener | 0.1 |
| Perfume delivery system (Example I) | 3.0 |
| Detersive enzyme (1:1 LIPOLASE/ESPERASE) | 1.0 |
| Sodium Sulphate | 15 |
| Water and fillers** | Balance to 100% |

**Can be selected from convenient materials such as CaCO₃, talc, clay, silicates, and the like.

An aqueous crutcher mix of heat and alkali stable components of the detergent composition is prepared and spray-dried. The resulting granules are passed through a Lodige CB mixer until a density of 650 grams/liter is secured. The other ingredients, including the perfume delivery system, are admixed therewith so that the final composition contains the ingredients tabulated at the levels shown.

Testing is conducted following the testing methods in Example II. Fabrics laundered with the composition have a noticeable perfume fragrance after drying in an automatic dryer at 60°–70° C. for approximately 40 minutes.

What is claimed is:

1. A perfume delivery composition in the form of particles comprising:
    a) a solid, water-insoluble, porous carrier which comprises a natural or synthetic zeolite having a nominal pore size of at least about 6 Angstroms;
    b) a perfume which is releasably incorporated in the pores of said zeolite carrier to provide a perfumed zeolite; and
    c) a matrix coated on said perfume zeolite which comprises a water-soluble composition in which the perfume is substantially insoluble, comprising from about 30% to about 50%, by weight, of at least one solid polyol containing more than 3 hydroxyl moieties and from about 50% to about 70%, by weight, of a fluid diol or polyol in which the perfume is substantially insoluble and in which the solid polyol is substantially soluble.

2. A composition according to claim 1 wherein said fluid polyol or diol is selected from the group consisting of glycerol, ethylene glycol, and diglycerol.

3. A composition according to claim 1 wherein the solid polyol is selected from the group consisting of glucose, sorbitol, maltose, glucamine, sucrose, polyvinyl alcohol, starch, alkyl polyglycoside, sorbitan fatty ester, polyhydroxy fatty acid amides whose fatty acid moieties contain from about 1 to about 18 carbon atoms, and mixtures thereof.

4. A composition according to claim 1 wherein the zeolite has a nominal pore size of at least about 7 Angstroms and a particle size no larger than about 120 microns.

5. A composition according to claim 4 wherein the zeolite is Zeolite X or Zeolite Y.

6. A composition according to claim 4 wherein the perfume is selected from the group consisting of hexyl cinnamic aldehyde, benzyl benzoate, dihydromyrcenol, eugenol, heliotropin, coumarin, and mixtures thereof.

7. A composition according to claim 1 wherein the perfumed zeolite comprises from about 5% to about 30%, by weight, of the perfume.

8. A composition according to claim 7 wherein the perfumed zeolite comprises from about 5% to about 20% of the perfume.

9. A composition according to claim 1 wherein the perfume delivery composition is in the form of agglomerated particles, said agglomerated particles being dissociable in water and having an average size of from about 200 microns to about 1000 microns.

10. A composition according to claim 9 wherein the agglomerated particles have an average size of from about 400 microns to about 600 microns.

11. A composition according to claim 1 wherein the perfume further comprises a perfume fixative.

12. A perfume delivery composition derived by a process which comprises the steps of:
- (a) forming a perfumed zeolite by mixing porous, substantially dehydrated Zeolite X or Y with a perfume such that the perfume is incorporated into the pores of the zeolite;
- (b) forming a matrix by mixing a solid polyol containing more than 3 hydroxyl moieties with glycerol, ethylene glycol, or diglycerol to form a liquid; and
- (c) mixing the matrix (b) with the perfumed zeolite (a) until free flowing particles are formed.

* * * * *